United States Patent
Lee

(10) Patent No.: US 9,872,627 B2
(45) Date of Patent: Jan. 23, 2018

(54) METHOD AND DEVICE FOR DETECTING BLOOD FLOW RATE

(71) Applicants: Zoetek Inc., Taipei (TW); Ren-Guey Lee, Taipei (TW)

(72) Inventor: Ren-Guey Lee, Taipei (TW)

(73) Assignees: ZOETEK INC., Taipei (TW); Ren-Guey Lee, Taipei (TW)

( * ) Notice: Subject to any disclaimer, the term of this patent is extended or adjusted under 35 U.S.C. 154(b) by 0 days.

(21) Appl. No.: 15/133,786

(22) Filed: Apr. 20, 2016

(65) Prior Publication Data

US 2017/0303801 A1    Oct. 26, 2017

(51) Int. Cl.
*A61B 5/02*  (2006.01)
*A61B 5/0295*  (2006.01)
*A61B 5/026*  (2006.01)
*A61B 5/00*  (2006.01)

(52) U.S. Cl.
CPC .......... *A61B 5/0295* (2013.01); *A61B 5/0261* (2013.01); *A61B 5/681* (2013.01); *A61B 5/725* (2013.01)

(58) Field of Classification Search
None
See application file for complete search history.

(56) References Cited

U.S. PATENT DOCUMENTS

| | | | |
|---|---|---|---|
| 2009/0216132 A1* | 8/2009 | Orbach | A61B 5/021 600/485 |
| 2015/0223700 A1* | 8/2015 | Kirenko | A61B 5/0205 600/473 |
| 2015/0374245 A1* | 12/2015 | Szilagyi | A61B 5/14551 600/479 |
| 2016/0026212 A1* | 1/2016 | Lee | G06F 1/163 361/679.03 |

FOREIGN PATENT DOCUMENTS

TW    1517838 B    1/2016

OTHER PUBLICATIONS

Elgendi,M. On the Analysis of Fingertip Photoplethysmogram Signals. Curr Cardiol Rev. Feb. 2012;8(1):14-25.*

* cited by examiner

*Primary Examiner* — Ankit D Tejani
(74) *Attorney, Agent, or Firm* — Muncy, Geissler, Olds & Lowe, P.C.

(57) ABSTRACT

A method and device for detecting a blood flow rate are disclosed. The method comprises steps: providing a detection light source, and projecting a light of the detection light source onto a skin of a living body and reach a blood vessel; using a photo sensor to receive a plurality of polarized light beams which are formed by the light of the detection light source reflected by expanding or contracting the blood vessel, wherein the photo sensor respectively generates a first PPG signal and a second PPG signal in blood vessel expansion and contraction; using a microprocessor to acquire at least one first PPG signal and at least one second PPG signal, calculating an offset of received light beams and a time derivative thereof according to a sequence of the first PPG signal and the second PPG signal, and converting the offset and time derivative into a blood flow rate.

11 Claims, 7 Drawing Sheets

METHOD AND DEVICE FOR DETECTING BLOOD FLOW RATE

FIELD OF THE INVENTION

The present invention relates to a method and device for detecting a blood flow rate, particularly to a method and device using photoplethysmographics (PPG) to detect a blood flow rate.

BACKGROUND OF THE INVENTION

The blood flow rate is an important physiological parameter, and researchers have proposed many methods to measure the blood flow rate. With advance of medical technology, non-invasive measurement methods have gradually replaced the conventional invasive measurement methods. Among the non-invasive methods, the vascular visualizer and the Doppler ultrasonography are the most popularized technologies. However, the abovementioned two methods need bulky apparatuses and a lot of consumables. Thus, the application thereof is constrained.

With emergence of wearable devices, many consumers wear wearable devices to detect the physiological signals in real time. Owing to bulky volume, the users are unlikely to wear the current blood flow rate devices, including the vascular visualizer and the Doppler ultrasonography device.

A Taiwan patent No. 1517838 disclosed a blood flow sensing device, which comprises a sensing module, a comparing unit and a display unit, wherein two different areas of a testis or scrotum are respectively defined to be a comparison measurement area and a reference measurement area. The sensing module emits a light beam with a specified wavelength to the comparison measurement area and the reference measurement area and receives the light beams reflected from the comparison measurement area and the reference measurement area to obtain comparison pulse information, reference pulse information, comparison blood oxygen concentration and reference blood oxygen concentration. The comparing unit respectively compares the comparison pulse information and the comparison blood oxygen information with the reference pulse information and the reference blood oxygen information to output a relative blood flow state of the blood vessels of the comparison measurement area and the reference measurement area. Next, the comparing unit determines the relative blocking state or disconnection state of the blood vessels of the comparison measurement area and the reference measurement area according to the relative blood flow state. Then, the display unit presents the relative blood flow state. The abovementioned conventional technology needs multiple groups of sensors to measure the comparison measurement area and the reference measurement area at the same time. Further, there is a distance between the comparison measurement area and the reference measurement area. Both factors are unfavorable to the application to wearable devices. Besides, the conventional technology cannot learn the blood flow rate but can only obtain the blood flow state.

SUMMARY OF THE INVENTION

The primary objective of the present invention is to provide a method and device for detecting a blood flow rate, which are applicable to a wearable device and easy to operate.

To achieve the abovementioned objective, the present invention proposes a method for detecting a blood flow rate, which comprises Step 1: providing a detection light source, and projecting a light of the detection light source onto a skin of a living body in a detection duration to pass through the skin and reach a blood vessel;

Step 2: using a photo sensor to receive a plurality of polarized light beams which are formed by the light of the detection light source reflected by expanding or contracting the blood vessel, detecting a first polarization angle of one of the plurality of polarized light beams reflected to the photo sensor during the blood vessel expansion to generate a first photoplethysmographic (PPG) signal, and detecting a second polarization angle of another one of the plurality of polarized light beams reflected to the photo sensor during the blood vessel contraction to generate a second photoplethysmographic (PPG) signal, wherein the second polarization angle is different from the first polarization angle; and Step 3: using a microprocessor to acquire at least one first PPG signal and at least one second PPG signal in the detection duration, working out an offset of the received light beams and a time derivative of the offset according to a sequence of the first PPG signal and the second PPG signal, and using the offset of the received light beams and the time derivative of the offset to work out a blood flow rate.

In one embodiment, Step 1 further comprises a sub-step: persistently projecting the light of the detection light source with a projection light frequency onto the skin of the living body in the detection duration.

In one embodiment, Step 1 further comprises a sub-step: providing a complementary light source, and persistently projecting a light of the complementary light source onto the skin of the living body in the detection duration.

In one embodiment, the photo sensor includes a plurality of photo sensing units; a polarized light beam reflected by the expanding blood vessel or the contracting blood vessel is projected onto one of the photo sensing units; the photo sensing unit receiving the polarized light beam generates the first PPG signal or the second PPG signal.

In one embodiment, Step 2 further comprises a sub-step: filtering the first PPG signal or the second PPG signal.

In one embodiment, Step 2 further comprises a sub-step: using the microprocessor to enable a portion of the photo sensing units to receive the polarized light beam reflected by the expanding blood vessel or the contracting blood vessel and to disable the rest of the photo sensing units.

The present invention also proposes a device for detecting a blood flow rate, which comprises a device body, a light source generator, and a microprocessor. The device body includes a detection area disposed corresponding to a skin of a living body. The light source generator is arranged inside the device body and exposed to the detection area. The light source generator is enabled to generate a light of a detection light source and project the light of the detection light source onto the skin, whereby the light of the detection light source passes through the skin and reaches a blood vessel. A photo sensor is arranged inside the device body and exposed to the detection area. The photo sensor is enabled to detect the polarized light beam reflected by the blood vessel during blood vessel expansion or blood vessel contraction. During blood vessel expansion, the photo sensor receives a polarized light beam reflected at a first polarization angle to generate a first PPG signal. During blood vessel contraction, the photo sensor receives another polarized light beam reflected at a second polarization angle to generate a second PPG signal. The microprocessor is arranged inside the device body and connected with the light source generator and the photo sensor. The microprocessor receives at least one first PPG signal and at least one second PPG signal from the photo sensor. The microprocessor uses the sequence of the first PPG signal and the second PPG signal to work out an offset of the received light beams and a time derivative of the offset and then to convert the offset and the time derivative of the offset into a blood flow rate.

In one embodiment, the device further comprises a filtering element connected with the photo sensor and filtering the first PPG signal and the second PPG signal; and an analog/digital converter bridging the filtering element and the microprocessor.

In one embodiment, the device further comprises a complementary light source generator arranged inside the device body and exposed to the detection area; the complementary light source generator works synchronously with the light source generator and projects a light of the complementary light source onto the skin of the living body. In one embodiment, the light of the complementary light source is a white light beam.

In one embodiment, the photo sensor further comprises a plurality of light sensing units. In one embodiment, the light sensing units are arranged into an array.

In one embodiment, the device further comprises a switch connected with the microprocessor and the photo sensing units and controlled by the microprocessor to enable or disable a portion of the photo sensing units.

Compared with the conventional technologies, the present invention is characterized in:

Using the light source generator to project the light of the detection light source onto the skin of the living body;

Using the photo sensor to receive the polarized light beam reflected by the expanding blood vessel or the contracting blood vessel, which illuminated by the light of the detection light source, and acquire the first PPG signal and the second PPG signal; and Using the microprocessor to work out the offset of the received light beams and the time derivative of the offset according to the sequence of the first PPG signal and the second PPG signal and convert the offset of the received light beams and the time derivative of the offset into a blood flow rate.

Thereby, the device of the present invention is simpler in structure and applicable to a wearable device. Further, the method of the present invention uses a simpler computation process to acquire the blood flow rate.

DETAILED DESCRIPTION OF THE PREFERRED EMBODIMENTS

The technical contents of the present invention will be described in detail in cooperation with drawings below.

Figure 1:
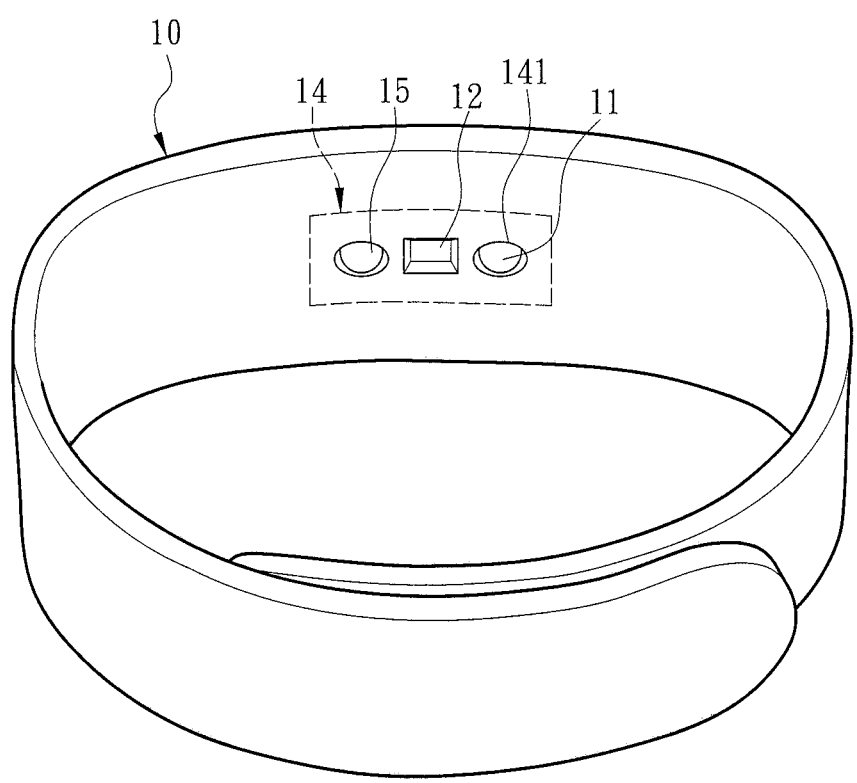
FIG. 1 is a perspective view schematically showing the appearance of a device for detecting a blood flow rate according to one embodiment of the present invention.
Figure 2:
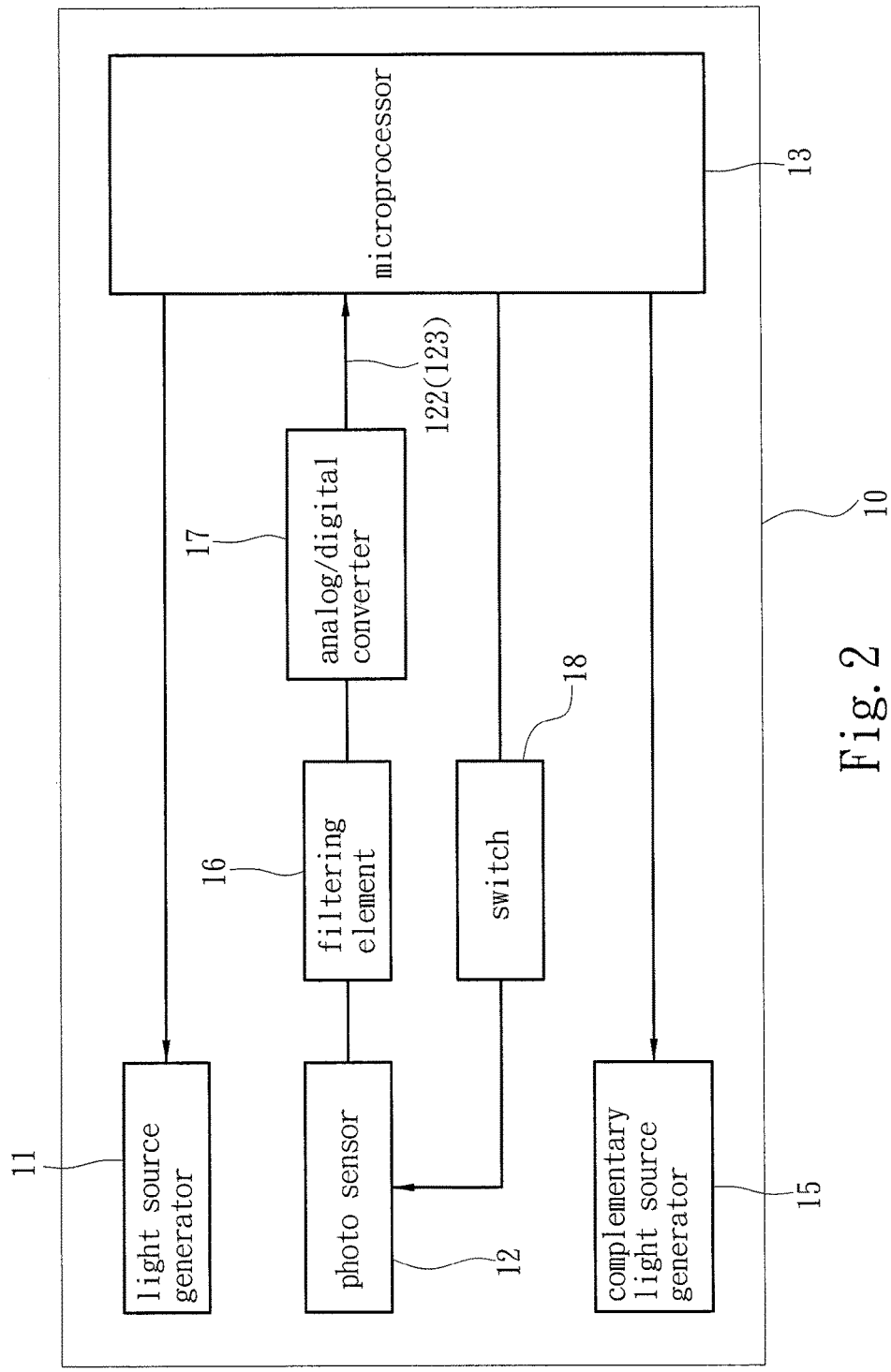
FIG. 2 is a block diagram schematically showing the components of a device for detecting a blood flow rate according to one embodiment of the present invention.

Refer to FIG. 1 and FIG. 2. The present invention proposes a method and device for detecting a blood flow rate. The device of the present invention comprises a device body 10, a light source generator 11, a photo sensor 12, and a microprocessor 13.

The device of the present invention may be a wearable device, such as a smart bracelet or a smart watch. The structure of the device of the present invention is designed according to practical application. The device body 10 accommodates the light source generator 11, the photo sensor 12 and the microprocessor 13 there inside. A region of the device body 10 is defined to be a detection area 14. At least two through-holes 141 are formed in the detection area 14, respectively provided the light source generator 11 and the photo sensor 12 therein, whereby the light source generator 11 and the photo sensor 12 are exposed from the through-holes 141. Besides, the detection area 14 is corresponding to a skin 2 of a living body. Thus, the device of the present invention is compliantly attached to the skin 2 in measurement. After being enabled, the light source generator 11 generates a light of a detection light source 111, which is an invisible infrared light beam. The wavelength of the infrared light beam can be adjusted according to requirement of detection, such as 660 nm or 940 nm.

Figure 3:
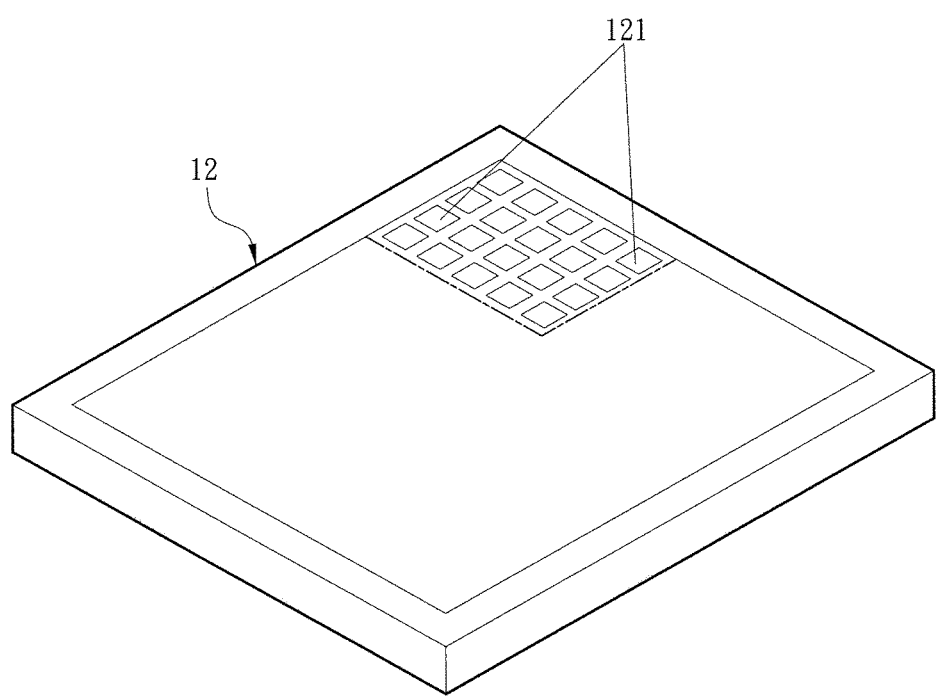
FIG. 3 is a diagram schematically showing the structure of a photo sensor of a device for detecting a blood flow rate according to one embodiment of the present invention.

After being enabled, the photo sensor 12 receives a plurality of polarized light beams which are formed by the light of the detection light source 111 reflected by a object and undertakes a photoelectric reaction to generate an electric signal. Refer to FIG. 3. In one embodiment, the photo sensor 12 includes a plurality of photo sensing units 121. Each photo sensing unit 121 can receive each polarized light beam which is formed by the light of the detection light source 111 reflected by the object and convert each polarized light beam into an electric signal. In one embodiment, the photo sensing units 121 are arranged into an array, and a spacing exists between each two adjacent photo sensing units 121.

The microprocessor 13 is connected with the light source generator 11 and the photo sensor 12. The microprocessor 13 is configured to include at least one working mode determining whether to enable the light source generator 11 and the photo sensor 12. The microprocessor 13 receives the electric signal generated by the photo sensor 12, and processes and analyzes the electric signal to obtain a blood flow rate.

Figure 4:
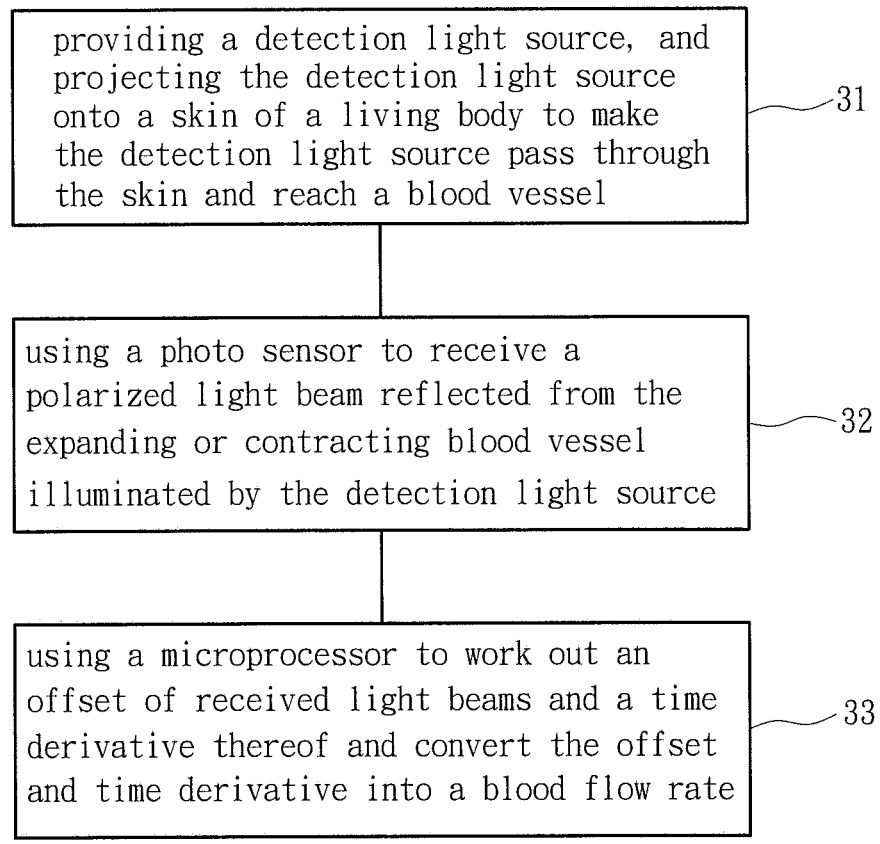
FIG. 4 is a flowchart of a method for detecting a blood flow rate according to one embodiment of the present invention.

Refer to FIG. 4. The method for detecting a blood flow rate of the present invention comprises Steps 1-3.

In Step 1 (31), provide a detection light source 111, and project a light of the detection light source 111 onto a skin 2 of a living body to make the light of the detection light source 111 pass through the skin 2 and reach a blood vessel 21 in a detection duration.

In Step 2 (32), use a photo sensor 12 to receive a plurality of polarized light beams which are formed by the light of the detection light source 111 reflected by expanding or contracting the blood vessel 21. While the blood vessel 21 is expanding, the light of the detection light source 111 is reflected to the photo sensor 12 at a first polarization angle 112, whereby the photo sensor 12 generates a first PPG signal 122. While the blood vessel 21 is contracting, the light of the detection light source 111 is reflected to the photo sensor 12 at a second polarization angle 113, wherein the second polarization angle 113 is different from the first polarization angle 112, whereby the photo sensor 12 generates a second PPG signal 123.

In Step 3 (33), use a microprocessor 13 to acquire at least one first PPG signal 122 and at least one second PPG signal 123 in the detection duration, work out an offset of the received light beams and a time derivative of the offset according to a sequence of the first PPG signal 122 and the second PPG signal 123, and convert the offset of the received light beams and the time derivative of the offset into a blood flow rate.

Figure 5:
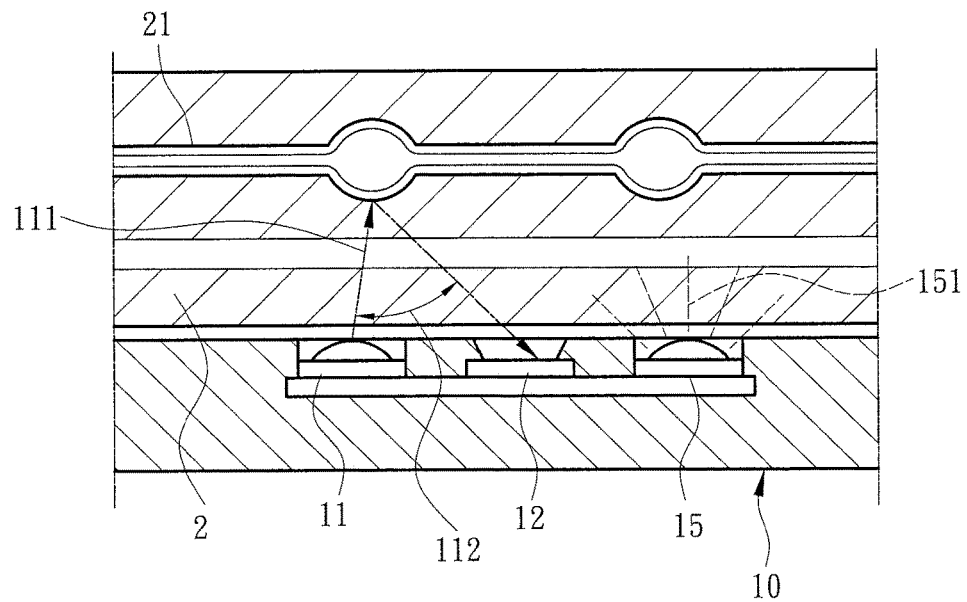
FIG. 5 is a diagram schematically showing the operation of a device for detecting a blood flow rate according to one embodiment of the present invention.
Figure 6:
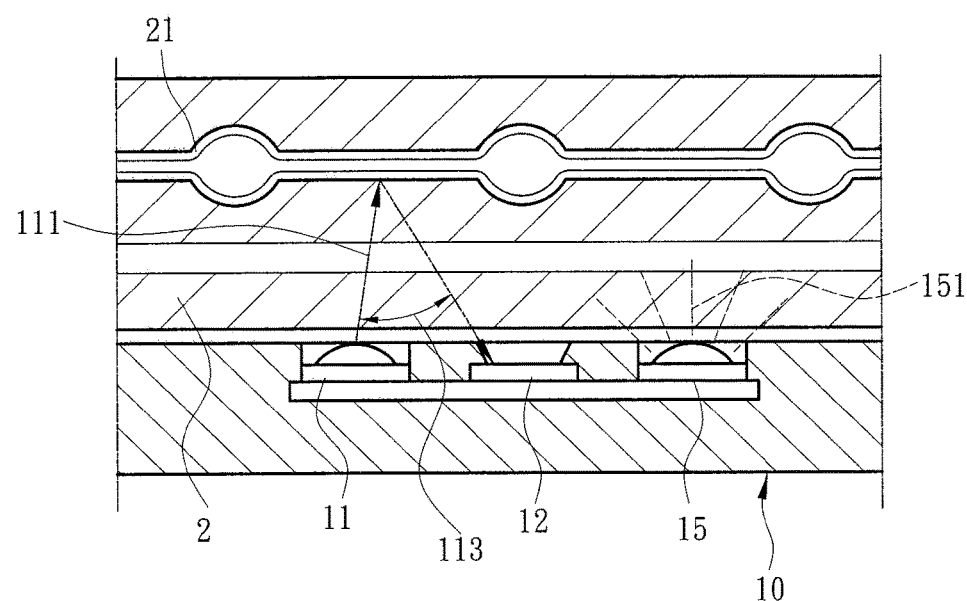
FIG. 6 is another diagram schematically showing the operation of a device for detecting a blood flow rate according to one embodiment of the present invention.

Refer to FIG. 5 and FIG. 6. Below is described the detail of the method of the present invention. Firstly, the detection area 14 of the device body 10 is placed on the skin 2 of the living body to be detected. For example, the detection area 14 of the device body 10 is placed on the wrist or breast of a human body. Meanwhile, the light source generator 11 and the photo sensor 12 are faced to the skin 2 of the living body. Next, let the microprocessor 13 begin to count the detection time, for example, 5 seconds, and enable the light source generator 11 and the photo sensor 12, whereby the light source generator 11 projects the light of the detection light source 111 onto the skin 2 of the living body. The light of the detection light source 111 passes through the skin 2 and reaches the blood vessel 21. Then, the process proceeds to Step 2 (32). It should be noted: the light of the detection light source 111 is always projected onto an identical position of the skin 2 during the detection process.

Figure 7:
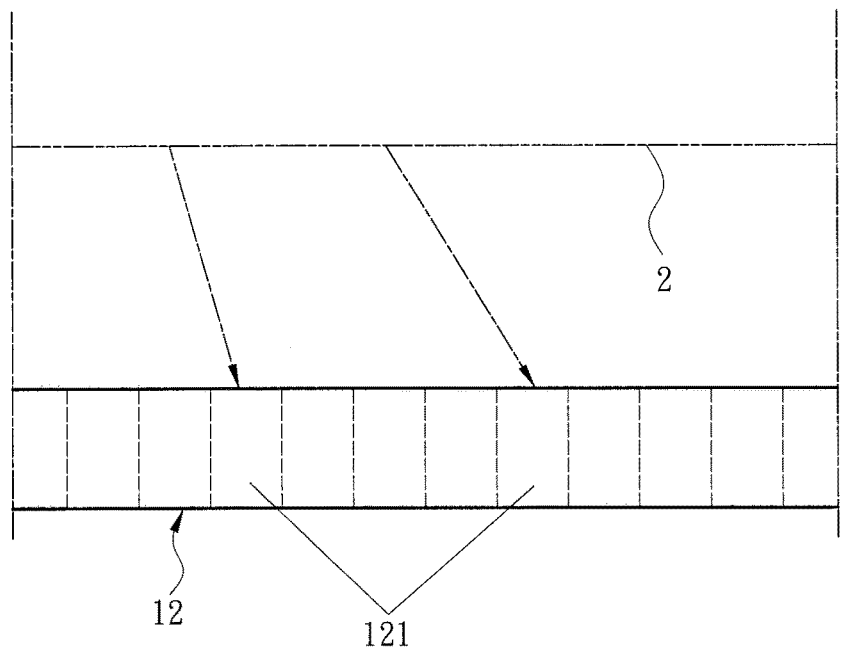
FIG. 7 is a local view schematically showing the reflection of light beams in a device for detecting a blood flow rate according to one embodiment of the present invention.

Step 2 (32) is still in the detection duration, and the microprocessor 13 keeps on enabling the light source generator 11 to project the light of the detection light source 111 onto the skin 2 of the living body and enabling the photo sensor 12 to receive the plurality of polarized light beams which are formed by the light of the detection light source 111 reflected by expanding or contracting the blood vessel 21. Suppose that the blood vessel 21 is expanding at initiation of detection. Acted on by the vascular wall, the light of the detection light source 111 is reflected to the photo sensor 12 at a first polarization angle 112. The photo sensor 12 thus generates a first PPG signal 122. Later, the blood vessel 21 shifts from expansion to contraction. Acted on by the variation of the vascular wall, the light of the detection light source 111 is reflected to the photo sensor 12 at a second polarization angle 113, which is different from the first polarization angle 112. The photo sensor 12 thus generates a second PPG signal 123. Refer to FIG. 7. In one embodiment, the photo sensor 12 includes a plurality of photo sensing units 121; during blood vessel expansion, the light of the detection light source 111 is reflected to one of the photo sensing units 121 at the first polarization angle 112; during blood vessel contraction, the light of the detection light source 111 is reflected to another one of the photo sensing units 121 at the second polarization angle 113, which is different from the first polarization angle 112. Thus, different photo sensing units 121 respectively generate the first PPG signal 122 and the second PPG signal 123. Then, the process proceeds to Step 3 (33).

In Step 3 (33), the microprocessor 13 acquires at least one first PPG signal 122 and at least one second PPG signal 123 in the detection duration and the microprocessor 13 arranges each pair of successive the first PPG signal 122 and the second PPG signal 123 as a test group. The microprocessor 13 analyzes the first PPG signal 122 and the second PPG signal 123 of the test group to obtain the offset of the received light beams and the time derivative of the offset. In order to enhance the reliability of detection, the plurality of test groups is analyzed statistically before the detection result is output. As mentioned above, two different photo sensing units 121 respectively receive the light of the detection light sources 111 reflected at different angles and generate the first PPG signal 122 and the second PPG signal 123. The present invention further calculates a distance difference between the two photo sensing units 121 to acquire the offset of the received light beams. Furthermore, the microprocessor 13 calculates the time derivative between the time point at which the first PPG signal 122 is generated and the time point at which the second PPG signal 123 is generated and then acquires the offset change with respect to time, i.e. the time derivative of the offset. Then, the microprocessor 13 undertakes the computation of the offset of the received light beams and the time derivative of the offset and divides the offset of the received light beams by the time derivative of the offset to obtain the blood flow rate.

Figure 8:
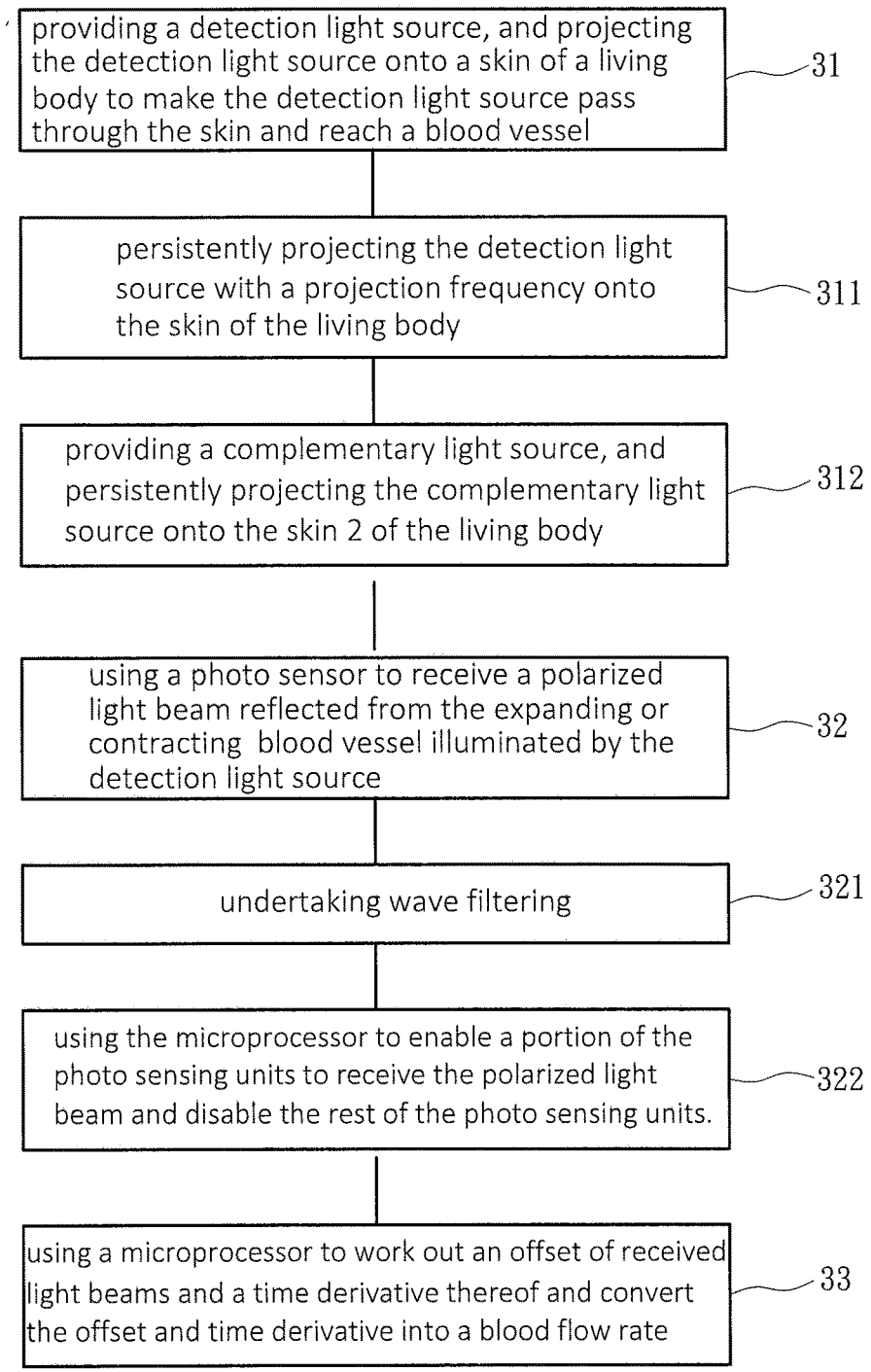
FIG. 8 is a flowchart of a method for detecting a blood flow rate according to another embodiment of the present invention.

Refer to FIG. 8. In one embodiment, Step 1 (31) further comprises Sub-Step 311: persistently projecting the light of the detection light source 111 with a projection frequency onto the skin 2 of the living body in the detection duration. In detail, the microprocessor 13 controls the light source generator 11 to persistently project the light of the detection light source 111 with the projection frequency onto the skin 2 of the living body, wherein the projection frequency is adjusted according to the practical requirement of detection.

In one embodiment, the device of the present invention further comprises a complementary light source generator 15, which is disposed in the device body 10 and exposed to the detection area 14, to enable the photo sensor 12 to more effectively sense the reflected light of the detection light source 111. The complementary light source generator 15 is electrically connected with the microprocessor 13 and controlled by the microprocessor 13. The complementary light source generator 15 is configured to operate synchronously with the light source generator 11 and project a light of a complementary light source 151 onto the skin 2 of the living body. In one embodiment, the light of the complementary light source 151 is a tiny beam of white light. The light of the complementary light source 151 is used to make the photoelectric structure of the photo sensor 12 enter the working state before the photo sensor 12 receives the light of the detection light source 111, whereby the photo sensor 12 is exempted from the influence of the environmental light and able to effectively sense the light of the detection light source 111. Correspondingly, in one embodiment, Step 1 (31) further comprises Sub-Step 312: providing the complementary light source 151, and persistently projecting the light of the complementary light source 151 onto the skin 2 of the living body in the detection duration.

Refer to FIG. 8 again. In one embodiment, Step 2 (32) further comprises Sub-Step 321: filtering the first PPG signal 122 and the second PPG signal 123. Correspondingly, in one embodiment, the device of the present invention further comprises a filtering element 16 disposed inside the device body 10 and connected with the photo sensor 12. The filtering element 16 receives every first PPG signal 122 and every second PPG signal 123 generated by the photo sensor 12 and undertakes wave filtering of every first PPG signal 122 and every second PPG signal 123 so as to guarantee the information processing quality in the succeeding process. In the present invention, the wave filtering may be band-pass filtering or low-pass filtering according to requirement in practical application. However, the present invention does not limit that the wave filtering mast be band-pass filtering or low-pass filtering. In one embodiment, the device of the present invention further comprises an analog/digital converter 17 bridging the filtering element 16 and the microprocessor 13. The analog/digital converter 17 converts the first PPG signal 122 and the second PPG signal 123 from analog signals into digital signals processed by the microprocessor 13.

In one embodiment, Step 2 (32) further comprises Sub-Step 322: using the microprocessor 13 to enable a portion of the photo sensing units 121 to receive the polarized light beam reflected by expanding the blood vessel 21 or contracting the blood vessel 21, which is illuminated by the light of the detection light source 111, and to disable the rest of the photo sensing units 121. In one embodiment, the photo sensor 12 includes a plurality of photo sensing units 121, and the device of the present invention further comprises a switch 18 to specifically control every photo sensing unit 121, wherein the switch 18 is connected with the microprocessor 13 and the photo sensing units 121 and controlled by the microprocessor 13 to enable or disable a portion of the photo sensing units 121. For example, the microprocessor 13 controls the switch 18 to enable the photo sensing units 121 arranged in an identical row and disable the rest of the photo sensing units 121. Thereby, the calculation of the offset of the received light beams is simplified.

What is claimed is:

1. A method for detecting a blood flow rate, comprising the steps of:
    Step 1: providing a detection light source, and projecting a light of the detection light source onto a skin of a living body to make the light pass through the skin and reach a blood vessel in a detection duration;
    Step 2: using a photo sensor comprising: a plurality of photo sensing units to receive a plurality of polarized light beams composing the light of the detection light source reflected by expanding or contracting the blood vessel at different angles, respectively, wherein each of the plurality of polarized light beams are projected to different photo sensing units of the plurality of photo sensing units for reflecting at the different angles, and wherein while the blood vessel is expanding, the polarized light beam is reflected at a first polarization angle to one of the plurality of photo sensing units of the photo sensor to generate a first photoplethysmographic (PPG) signal, and wherein while the blood vessel is contracting, the polarized light beam is reflected at a second polarization angle to another one of the photo sensing units of the photo sensor to generate a second PPG signal, wherein the second polarization angle is different from the first polarization angle; and
    Step 3: using a microprocessor to acquire at least one first PPG signal and at least one second PPG signal in the detection duration, working out an offset of received light beams by calculating a distance between the two photo sensing units which generate the first PPG signal and the second PPG signal, and receiving a time derivative of the offset according to a sequence of the first PPG signal and the second PPG signal, and further using the microprocessor to convert the offset of received light beams and the time derivative of the offset into a blood flood flow rate.

2. The method for detecting a blood flow rate according to claim 1, wherein Step 1 further comprises a sub-step: persistently projecting the light of the detection light source with a projection frequency onto the skin of the living body in the detection duration.

3. The method for detecting a blood flow rate according to claim 1, wherein Step 1 further comprises a sub-step: providing a complementary light source, and persistently projecting a light of the complementary light source onto the skin of the living body in the detection duration.

4. The method for detecting a blood flow rate according to claim 1, wherein Step 2 further comprises a sub-step: filtering the first PPG signal and the second PPG signal.

5. The method for detecting a blood flow rate according to claim 1, wherein Step 2 further comprises a sub-step: using the microprocessor to enable a portion of the photo sensing units to receive the plurality of the polarized light beams composing the light of the detection light source reflected by expanding the blood vessel or contracting the blood vessel, and to disable the photo sensing units not in the portion enabled to receive the polarized light beams.

6. A device for detecting a blood flow rate, comprising
    a device body including a detection area, which is corresponding to a skin of a living body;
    a light source generator disposed inside the device body and exposed to the detection area, the light source generator enabled to generate a light of a detection light source projected onto the skin of the living body, wherein the light of the detection light source passes through the skin of the living body and reaches a blood vessel in the skin of the living body, wherein the light of the detection light source is composed of a plurality of polarized light beams;
    a photo sensor, comprising: a plurality of photo sensing units arranged in an array, disposed inside the device body and exposed to the detection area, at least two of the plurality of photo sensing units enabled to receive at least two of the plurality of polarized light beams reflected by expanding or contracting the blood vessel at different angles, respectively, wherein each of the plurality of polarized light beams are protected to different photo sensing units of the plurality of photo sensing units for reflection at the different angles, and wherein while the blood vessel is expanding, one of the plurality of photo sensing units of the photo sensor receives one polarized light beam of the plurality of polarized light beams which is reflected at a first polarization angle and generates a first photoplethysmographic (PPG) signal, and wherein while the blood vessel is contracting, another one of the photo sensing units of the photo sensor receives another polarized light beam of the plurality of polarized light beams reflected at a second polarization angle which generates a second PPG signal; and
    a microprocessor disposed inside the device body and connected with the light source generator and the photo sensor, the microprocessor receiving at least one first PPG signal and at least one second PPG signal from the photo sensor, working out an offset of received light beams by calculating a distance between the two photo sensing units which generate the first PPG signal and the second PPG signal, and receiving a time derivative of the offset according to a sequence of the first PPG signal and the second PPG signal, and further using the microprocessor to calculate and convert the offset of the received light beams and the time derivative of the offset into a blood flow rate.

7. The device for detecting a blood flow rate according to claim 6 further comprising a filtering element, which is disposed inside the device body and connected with the photo sensor for filtering the first PPG signal and second PPG signal; and an analog/digital converter, which bridges the filtering element and the microprocessor.

8. The device for detecting a blood flow rate according to claim 6 further comprising a complementary light source generator, which is disposed in the device body and exposed in the detection area, and which operates synchronously with the light source generator and projects a light of a complementary light source onto the skin of the living body.

9. The device for detecting a blood flow rate according to claim 8, wherein the light of the complementary light source is a white light beam.

10. The device for detecting a blood flow rate according to claim 6, wherein the photo sensing units are arranged into an array.

11. The device for detecting a blood flow rate according to claim 6 further comprising a switch, which is connected with the microprocessor and the photo sensing units and controlled by the microprocessor to enable or disable a portion of the photo sensing units.

\* \* \* \* \*